(12) United States Patent
Atkins et al.

(10) Patent No.: US 12,179,134 B2
(45) Date of Patent: Dec. 31, 2024

(54) HYBRID METHOD FOR CARBON CAPTURE

(71) Applicant: CARBON HOLDINGS INTELLECTUAL PROPERTIES, LLC, Lexington, KY (US)

(72) Inventors: Charles Agee Atkins, Sheridan, WY (US); Christopher L Yurchick, McDonald, PA (US); Charles Hill, Lexington, KY (US); Robert McDowell, Lexington, KY (US)

(73) Assignee: CARBON HOLDINGS INTELLECTUAL PROPERTIES, LLC, Ranchester, WY (US)

( * ) Notice: Subject to any disclaimer, the term of this patent is extended or adjusted under 35 U.S.C. 154(b) by 39 days.

(21) Appl. No.: 17/733,750

(22) Filed: Apr. 29, 2022

(65) Prior Publication Data

US 2022/0347612 A1 Nov. 3, 2022

Related U.S. Application Data

(60) Provisional application No. 63/182,332, filed on Apr. 30, 2021.

(51) Int. Cl.
*B01D 39/20* (2006.01)
*B01J 12/00* (2006.01)
*B01J 20/20* (2006.01)
*B01J 23/46* (2006.01)
*B01J 23/72* (2006.01)
(Continued)

(52) U.S. Cl.
CPC ........ *B01D 39/2062* (2013.01); *B01J 12/007* (2013.01); *B01J 20/20* (2013.01); *B01J 23/462* (2013.01); *B01J 23/72* (2013.01); *B01J 27/051* (2013.01); *C07C 1/12* (2013.01); *B01D 2253/102* (2013.01); *B01D 2253/308* (2013.01); *B01D 2257/504* (2013.01)

(58) Field of Classification Search
CPC ........ B01D 39/06; B01D 39/20; B01D 53/02; B01D 53/04; B01D 53/32
See application file for complete search history.

(56) References Cited

U.S. PATENT DOCUMENTS

| 5,446,005 A | 8/1995 | Endo |
| 8,440,729 B2 | 5/2013 | Olah et al. |
| (Continued) | | |

FOREIGN PATENT DOCUMENTS

DE  102016005418 A1  11/2017

OTHER PUBLICATIONS

Ali et al. "Graphene-based Membranes for CO2 Separation." Materials Science for Energy Technologies. vol 2. (2019) 83-88 (Year: 2019).*

(Continued)

*Primary Examiner* — Sharon Pregler
(74) *Attorney, Agent, or Firm* — Dorsey & Whitney LLP

(57) ABSTRACT

A method of removing carbon dioxide from a gas can include providing a gaseous feed stream including a carbon dioxide gas and adsorbing the carbon dioxide gas with a porous carbon sorbent. The method can further include de-adsorbing the carbon dioxide and combining the carbon dioxide with a substantially pure hydrogen gas to produce at least one of methane and methanol. The adsorbing and de-adsorbing of the carbon dioxide gas can be conducted by an electric swing adsorption.

8 Claims, 7 Drawing Sheets

(51) Int. Cl.
*B01J 27/051* (2006.01)
*C07C 1/12* (2006.01)

(56) References Cited

U.S. PATENT DOCUMENTS

| | | | | |
|---|---|---|---|---|
| 8,710,106 | B2* | 4/2014 | Junaedi | C07C 1/12 |
| | | | | 518/715 |
| 9,610,546 | B2* | 4/2017 | Sinton | B01D 53/228 |
| 2011/0268618 | A1* | 11/2011 | Finkenrath | B01D 53/62 |
| | | | | 96/9 |
| 2015/0059573 | A1 | 3/2015 | Filippi | |
| 2015/0360164 | A1* | 12/2015 | Carruthers | C12M 47/18 |
| | | | | 502/437 |
| 2017/0088419 | A1 | 3/2017 | Wynn et al. | |
| 2017/0333834 | A1 | 11/2017 | Worsley et al. | |
| 2020/0048165 | A1 | 2/2020 | Duggal et al. | |

OTHER PUBLICATIONS

Ganesan et al. "Activated Graphene-derived Porous Carbon with Exceptional Gas Adsorption Properties." vol. 220. (2016) 21-27 (Year: 2016).*

International Search Report and Written Opinion for PCT Application No. PCT/US2022/027094 dated Oct. 6, 2022.

Jotheeswari Kothandaraman, et al. "Conversion of CO2 from Air into Methanol Using a Polyamine and a Homogeneous Ruthenium Catalyst." Journal of the American Chemical Society (2015).

* cited by examiner

HYBRID METHOD FOR CARBON CAPTURE

CROSS-REFERENCE TO RELATED APPLICATIONS

This application claims priority to U.S. Provisional Patent Application No. 63/182,332 filed on Apr. 30, 2021, the disclosure of which is incorporated herein, in its entirety, by this reference.

BACKGROUND

Coal has been mined and used for a variety of purposes for thousands of years. Since the industrial revolution, the primary use for coal has been to generate heat and energy to power homes, industry, and transportation. Coal initially found widespread use as a transportation fuel for trains during the industrial revolution, but the advent of cars and the discovery of large petroleum deposits near the turn of the twentieth century precipitated a shift towards the primacy of liquid, petroleum-based fuels for transportation.

Research on coal continued, however, and the basic chemistry of coal was well understood by at least the early twentieth century. Although significant research has been conducted on coal liquefaction for more than a century, this extensive prior work has overwhelmingly been focused on the development of transportation fuels. The use of coal to produce other materials of greater industrial relevance has yet to be fully explored. For example, carbon-based technologies have come to the fore in recent years, with rapid developments being made in in the commercialization of advanced carbon materials such as carbon fiber, graphene, graphite, and carbon nanotubes. As these advanced materials are increasingly used in mass produced, high volume applications, there is a need to quickly and economically supply large quantities of advanced carbon materials to manufacturers. Thus, while transportation fuels from coal are not viewed as a fruitful avenue for commercialization, there remains significant work to be done in developing processes to convert coal into the advanced carbon materials that will be instrumental in the economy of the future.

The use of coal as an energy source has also been historically linked to greenhouse gas emissions. Achieving meaningful reductions in greenhouse gas emissions will require a wide range of solutions, and carbon capture will play an important role. Carbon capture is the process by which carbon dioxide from power-plants, and other industrial activities that would otherwise be released into the atmosphere, is captured and stored. The Intergovernmental Panel on Climate Change estimates that fossil fuel power plants and large industrial facilities account for as much as 60 percent of global carbon emissions. Thus, the broad-based deployment of cost-effective carbon capture and storage would potentially make a massive impact on the world's greenhouse gas levels.

SUMMARY

A method of capturing carbon dioxide can include removing carbon dioxide from a gas. The method can include providing a gaseous feed stream including a carbon dioxide gas and adsorbing the carbon dioxide gas with a porous carbon sorbent. The method can further include de-adsorbing the carbon dioxide and combining the carbon dioxide with a substantially pure hydrogen gas to produce at least one of methane and methanol. In some embodiments, the gaseous feed stream includes at least one of a flue gas, an exhaust, and a furnace exhaust. The porous carbon sorbent can include a mesoporous structure. In some embodiments, the porous carbon sorbent includes an activated carbon including at least one of an activated carbon fiber, an activated charcoal, an activated graphene, a coal composite, and combinations thereof. In other embodiments, the porous carbon sorbent can include a carbon foam including an activated pitch.

In some embodiments, combining the carbon dioxide with a substantially pure hydrogen gas can be conducted in the presence of a catalyst. The catalyst can include at least one of molybdenum sulfide, ruthenium, or copper. In some embodiments, the adsorbing and de-adsorbing of the carbon dioxide gas can be conducted by an electric swing adsorption. The method of capturing carbon dioxide can also include passing the gaseous feed stream through a graphene-based membrane. The graphene based membrane includes at least one of a nanoporous single-layer graphene, a multi-layer graphene-based stacked laminate, and a mixed-matrix membrane.

In some embodiments, a carbon dioxide separation system can include a gaseous stream including carbon dioxide, an activated carbon filter, and an adsorption system. The activated carbon filter can include nanopores. The gaseous stream including carbon dioxide is configured to flow through at least a portion of the activated carbon filter. The activated carbon filter is configured to separate the gaseous stream into a carbon dioxide-rich stream and a carbon dioxide-depleted stream. In some embodiments, the adsorption system is configured to further separate the carbon dioxide-rich stream.

The nanopores can include a diameter from about 2 nanometers to about 6 nanometers. In some embodiments, the adsorption system further separates the carbon dioxide rich stream into a substantially pure carbon dioxide stream and a carbon dioxide-depleted stream by electric swing adsorption. The adsorption system can include an apparatus including a porous dielectric adsorbent material in between and in electrical communication with a first electrical conductor and a second electrical conductor. In other embodiments, the adsorption system further separates the carbon dioxide rich stream into a substantially pure carbon dioxide stream and a carbon dioxide-depleted stream by physical adsorption. The adsorption system can further separate the carbon dioxide rich stream into a substantially pure carbon dioxide stream and a carbon dioxide-depleted stream by chemical adsorption.

A method of producing carbon dioxide can include passing a carbon dioxide-containing gas through a graphene based membrane, preparing an apparatus including a porous dielectric adsorbent material in between and in electrical communication with a first electrical conductor and a second electrical conductor, applying an electric field across the porous dielectric adsorbent material, passing the carbon dioxide-containing gas into the porous dielectric adsorbent material, removing the electric field and releasing the carbon dioxide, and capturing the carbon dioxide. In some embodiments, the carbon dioxide couples to the first electrical conductor and the second electrical conductor. The electric field can include an applied voltage from about 1V to about 3V. The dielectric adsorbent material can include a non-conductive insulator. In some embodiments, capturing the carbon dioxide includes combining the carbon dioxide with a substantially pure hydrogen gas to produce at least one of methane and methanol.

Features from any of the disclosed embodiments can be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

Throughout the drawings, identical reference numbers can designate similar, but not necessarily identical, elements.

DETAILED DESCRIPTION

The methods and systems described herein are useful in treatment of gaseous streams including carbon dioxide ($CO_2$), which can be obtained in many ways. In particular, gaseous carbon dioxide streams include those produced by combustion, especially flue gas streams produced by combustion of hydrocarbon fuels. The various aspects of the present disclosure are described below with particular reference to such flue gas streams, but without intending to be limited to such streams, and can be applied to various environments, vehicles, buildings, and/or locations.

As used herein, "physical absorption" or "physisorption" means absorbing a product, in this case carbon dioxide, from a gaseous feed stream by passing the feed stream into a liquid which preferentially dissolves the carbon dioxide from the feed stream, removing the feed stream depleted of the absorbed product, and then recovering the carbon dioxide from the liquid such as by lowering the pressure over the liquid or by stripping the carbon dioxide out of the liquid, wherein the absorption of the carbon dioxide into the liquid does not involve a chemical reaction of the carbon dioxide.

As used herein, "chemical absorption" or "chemisorption" means absorbing a product, in this case carbon dioxide, from a gaseous feed stream by passing the feed stream into a liquid which contains a component with which the carbon dioxide preferentially reacts, removing the feed stream depleted of the absorbed product, and then recovering the carbon dioxide from the liquid such as by lowering the pressure over the liquid or by stripping the carbon dioxide out of the liquid, wherein the absorption of the carbon dioxide into the liquid involves a chemical reaction of the carbon dioxide with a component in the liquid.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

Figure 1:
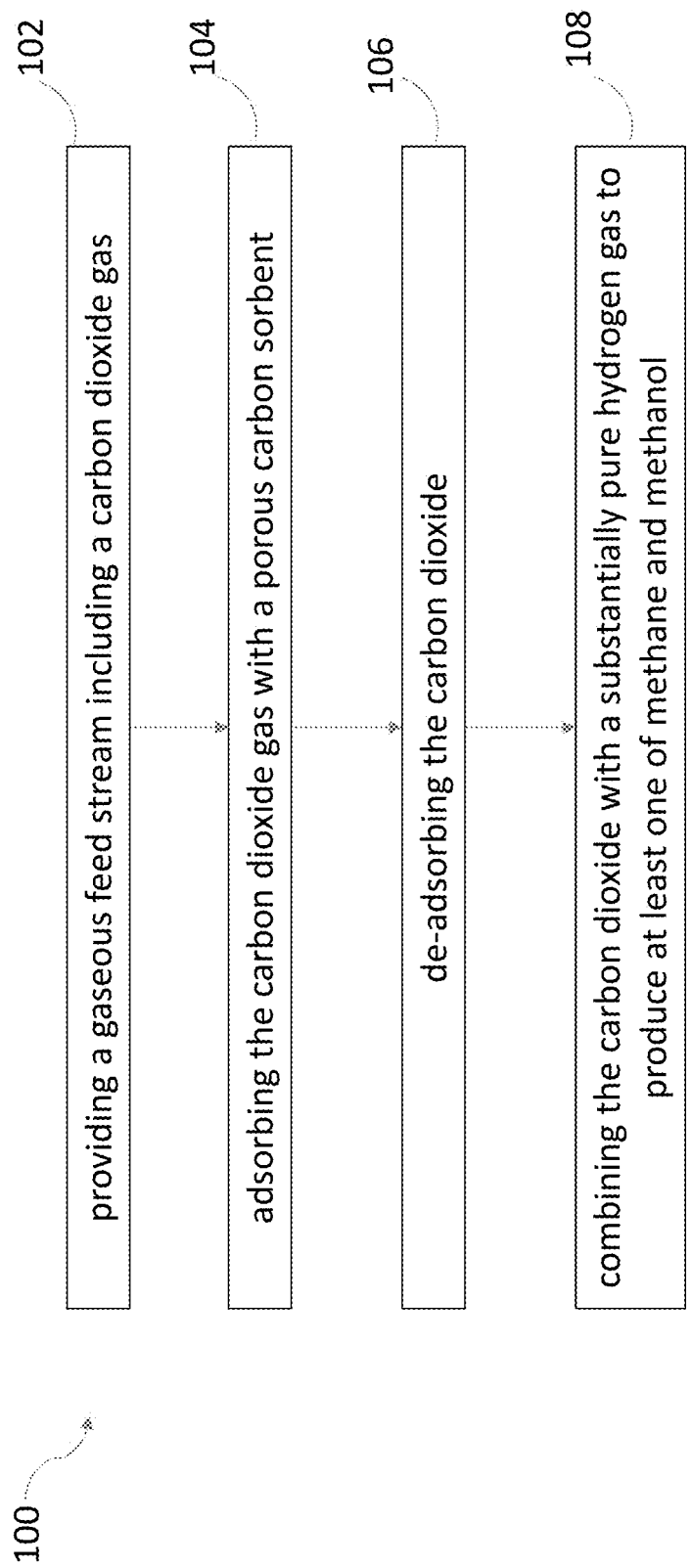
FIG. 1 illustrates a process flow diagram of a method of removing carbon dioxide from a gas mixture, according to an embodiment.

FIG. 1 illustrates a method 100 of removing carbon dioxide from a gas. The method 100 can include act 102 of providing a gaseous feed stream including a carbon dioxide gas and can further include a mixture of gases. In some embodiments, the gas can include a fluid gas stream from a power plant or industrial boiler. In other embodiments, the gas can include an exhaust from a vehicle or power generating machine, such as a natural gas or diesel generator, or a furnace exhaust. The gas can include various components including gases (e.g., $N_2$, $O_2$, $NO_x$, $SO_x$ etc.) and particulates (e.g., fly ash). A flue gas can typically also include heavy metals such as mercury (Hg) that must be removed from the flue gas prior to being released into the atmosphere. Greenhouse gases include carbon dioxide, methane, nitrous oxide, and other gases that accumulate in the atmosphere and create the heat-reflective layer. Although carbon dioxide is not the most effective greenhouse gas, it is considered the largest contributor to climate change because it is so common.

The method of removing carbon dioxide from a gas includes act 104 of adsorbing the carbon dioxide gas with a porous carbon sorbent. Adsorption can remove one or more components of a gaseous mixture with the help of a solid surface. The adsorption process can be based on significant intermolecular forces between the carbon dioxide and the surfaces of certain solid adsorbents such as carbon. Depending on the temperature, pressure and percentage of active loading, single or multiple layers of gases can be adsorbed.

In carbon dioxide capture by adsorption technology, carbon dioxide can be passed through a carbon sorbent. The carbon can be porous to increase the surface area. Carbon dioxide is attracted towards the adsorbent and adheres on the surface of adsorbent. After achieving equilibrium, act 106 of desorption to get carbon dioxide in pure form and regenerated sorbent can be performed. The regenerated sorbent can be utilized for further cycle. Solid sorbents have the potential for significant energy savings over liquid solvents, in part because they avoid the need for the large quantities of water that must be repeatedly heated and cooled to regenerate the solvent solution. Further, adsorption presents lower energy requirements and avoids the shortcomings when compared to absorption. In a post-combustion process, adsorption is recognized to be an attractive process for carbon dioxide capture from flue gases, due to its lower energy requirements.

Porous carbon-based materials have high thermal and chemical stability as well as good adsorption capabilities. The porous carbon sorbent can include an activated carbon. Activated carbon can be selected as the sorbent for the method because of some specific characteristics that it possesses: activated carbon preferentially adsorbs carbon dioxide over nitrogen, is mildly water resistant, and is relatively inexpensive. The combination of these factors make it a prime candidate for removal and purification of carbon dioxide from the flue gas of a coal-fired power plant.

The formation of pores and changes to the pore structure in activated carbon mostly occur during the activation process. Activation occurs when the carbon layers are etched away through an oxidation reaction resulting in the formation of a porous carbon network with high surface area. As the activation temperature increases, the raw material of the carbon undergoes pyrolysis. The residual carbon molecules re-aggregate into coke structures and form numerous mesopores and/or micropores. In some embodiments, the porous carbon sorbent includes a mesoporous structure. A mesoporous material is a material containing pores with diameters between 2 and 50 nm. Pore size, pore size distributions, and surface area, as well as pore surface chemistry are the major factors in the adsorption process. Higher activation temperatures can expedite pyrolysis reactions. Moreover, activated carbon is stable under acidic and basic conditions.

The method of removing carbon dioxide from a gas can also include an act 108 of combining the carbon dioxide with a substantially pure hydrogen gas to produce at least one of methane and methanol. A method of forming methanol by combining a mixture of methane, water and carbon dioxide under specific reaction conditions sufficient to form a mixture of hydrogen and carbon monoxide which are then reacted under conditions sufficient to form methanol can be achieve by various methods. U.S. Pat. No. 8,440,729, for example, describes a conversion of carbon dioxide to methanol using bi-reforming of methane or natural gas, the disclosure of which is incorporated, in its entirety, by this reference. Carbon dioxide can be directly converted into methanol using a homogeneous catalyst. Jotheeswari Kothandaraman, et al. "Conversion of $CO_2$ from Air into Methanol Using a Polyamine and a Homogeneous Ruthenium Catalyst." Journal of the American Chemical Society, the disclosure of which is incorporated, in its entirety, by this reference. In some embodiments, the combining of carbon dioxide with a substantially pure hydrogen gas can be conducted in the presence of a catalyst. The catalyst can include at least one of molybdenum sulfide, ruthenium, and/or copper. In other embodiments, the captured $CO_2$, which is nontoxic and inexpensive, can be used to produce various organic solvents, chemicals, and media materials (such as calcium carbonate, glucose, and starch), and thus it can potentially bring substantial commercial benefits.

Figure 2:
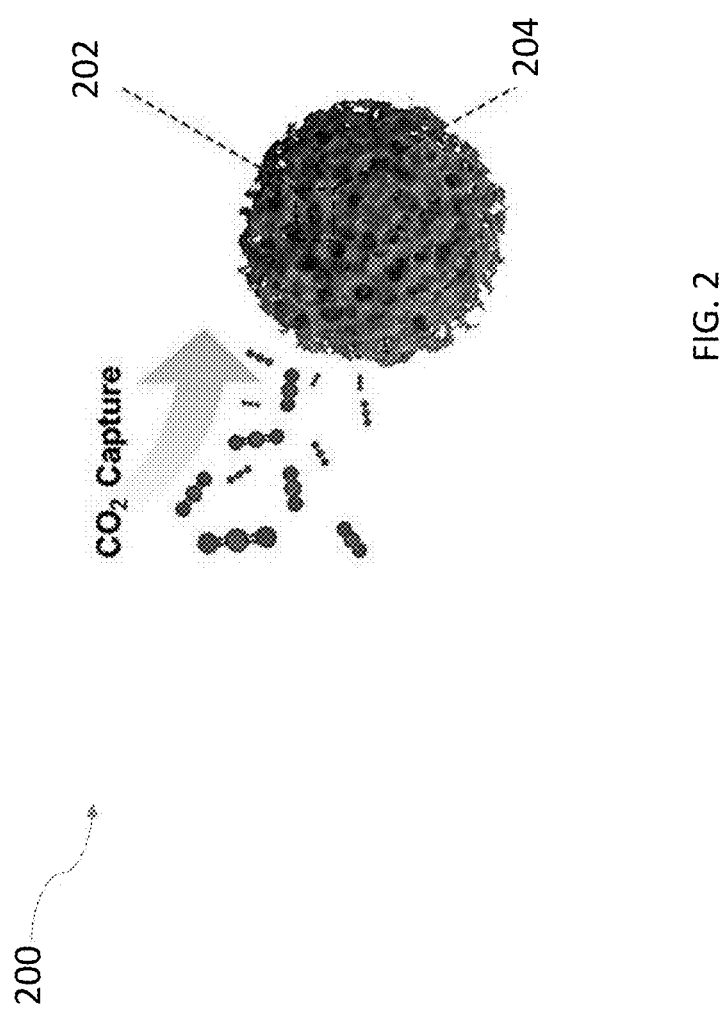
FIG. 2 illustrates a schematic of a porous carbon sorbent, according to an embodiment.

Referring to FIG. 2, in some embodiments, a carbon dioxide separation system 200 can include a gaseous stream including carbon dioxide and an activated carbon filter 202. The activated carbon filter 202 can include nanopores 204. The gaseous stream including carbon dioxide is configured to flow through at least a portion of the activated carbon filter 202 where the activated carbon filter 202 is configured to separate the gaseous stream into a carbon dioxide-rich stream and a carbon dioxide-depleted stream.

The activated carbon filter 202 can include a granular or a powdered block form that has been treated to be extremely porous. In some embodiments, a gram of activated carbon can have a surface area of 500 $m^2$ or higher. The nanopores 204 can include a diameter from about 2 nanometers to about 6 nanometers. The activated carbon filter 202 can include activated carbon fiber and/or granular activated carbon. In some embodiments, the activated carbon filter can include a graphene-based membrane.

The activated carbon filter 202 can include a porous carbon sorbent that includes an activated carbon including at least one of an activated carbon fiber, a bituminous-coal-based activated carbon, an activated charcoal, an activated graphene, a coal composite, and combinations thereof. Activated carbons have a large adsorption capacity, preferably for small molecules (e.g. carbon dioxide). By controlling the process of carbonization and activation, a variety of active carbons having different porosity can be obtained. Activated carbons are used mainly in granular and powdered forms, but can also be produced in textile form by controlled carbonization and activation of textile fibers. Activated carbon fibers include special characteristics such as fibrous structure, high porosity, high volumetric capacity, excellent packing density, fast adsorption kinetics, good porous storage capacity and ease of handling. Activated carbon fibers (ACFs) are more advantageous than other forms of activated carbon, as fibers have more uniform size and shape as a precursor to begin with. In addition, better diffusion between the fibers makes ACFs more suitable for adsorption applications. U.S. Pat. No. 5,446,005, for example, describes a pitch-based activated carbon fiber, the disclosure of which is incorporated, in its entirety, by this reference. Granular activated carbons (GAC) can be used primarily due to their low cost. The raw material for activated carbon can be any organic material with a high char yield (i.e. coal, peat, coconut shells, or certain polymers). Fibrous activated carbons (ACFs) offer a number of advantages over GACs, including greatly improved contact efficiency with the media leading to greater rates of adsorption, much higher surface areas (up to 2500 $m^2/g$) and the potential for greatly simplified in situ regeneration through electrical resistance heating. Activated graphene can include materials with a rigid 3D porous structure and high specific surface area.

In some embodiments, the activated carbon filter 202 can include a carbon foam. Carbon foam can be strong and lightweight, un-flammable and able to maintain its performance at high temperatures, and capable of absorbing carbon dioxide. In some embodiments, carbon foams can be produced from a variety of different materials, including asphalt, foamed synthetic plastic, and coal. Carbon foams constructed from a pitch can conduct heat well and have low density, but are comparatively weak. Coal-based foams are stronger and denser but do not conduct heat as well. Pitch based activated carbons (PAC) with a high specific surface area can be produced by a direct chemical activation. There are two common types of pitch that can be used for PAC production: petroleum pitch and coal-tar pitch. Petroleum pitch can be produced as a residue of crude oil distillation, and coal-tar pitch is a liquid product from the production of metallurgical coke. Because of its thermoplastic nature, pitch can be used for the production of all forms of activated carbon, including fibers, powders and granules. To produce ACFs, pitch is first melt-spun into small-diameter fibers. The resultant green fibers are then rendered infusible via oxidation to prevent them from melting and losing their shape during subsequent, higher-temperature, heat treatment steps.

The carbon dioxide separation system can also include an adsorption system 300 configured to further separate the carbon dioxide rich stream. Referring now to FIG. 3A, the adsorption system 300 further separates the carbon dioxide rich stream into a substantially pure carbon dioxide stream and a carbon dioxide-depleted stream by physical adsorption. The fundamental interacting force of physisorption is Van der Waals force. In comparison with chemisorption, in which the electronic structure of bonding atoms or molecules is changed and covalent or ionic bonds form, physisorption does not result in changes to the chemical bonding structure.

Physical adsorption can be suitable for the insoluble adsorption process in the adsorbent but only to the surface 302 only. Surfaces left by adsorbant 304 can be replaced by other adsorbant (multilayer). $CO_2$ adsorption can occur by chemical adsorption if a chemical reaction occurs at the exposed surface or by physical adsorption. In physisorption the $CO_2$ is adsorbed weakly by the substrate itself, in chemisorption, the $CO_2$ is adsorbed more strongly by specific binding sites.

Figure 3B:
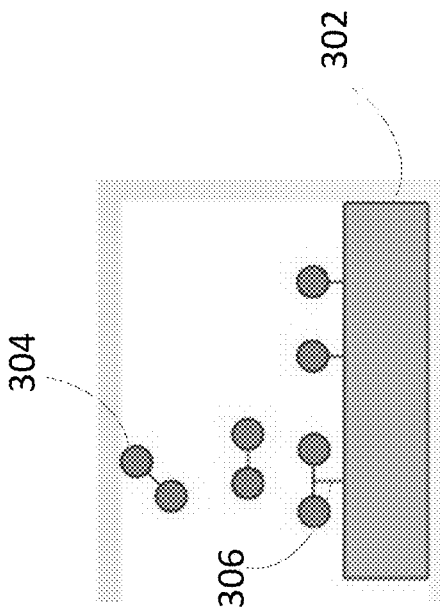
FIG. 3B illustrates a schematic view of an adsorption system including chemical adsorption, according to an embodiment.
Figure 3A:
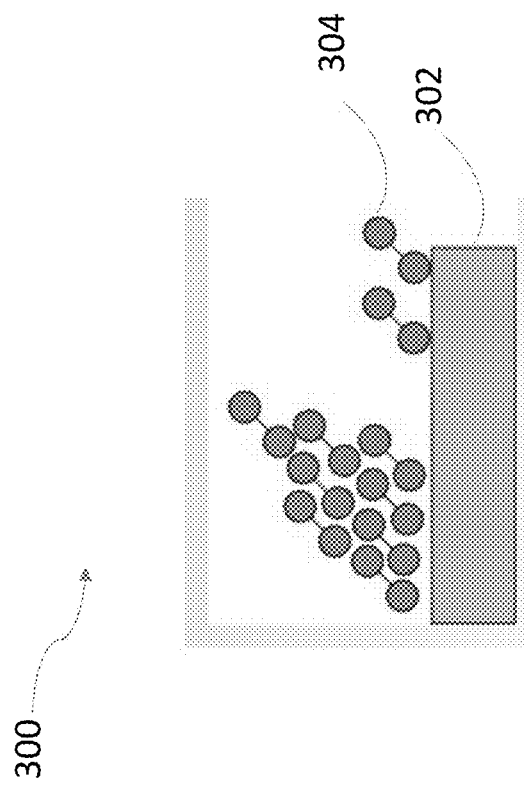
FIG. 3A illustrates a schematic view of an adsorption system including physical adsorption, according to an embodiment.

FIG. 3B illustrates the adsorption system 300 can further separates the carbon dioxide rich stream into a substantially pure carbon dioxide stream and a carbon dioxide-depleted stream by chemical adsorption. Chemisorption is a kind of adsorption which involves a chemical reaction between the surface 302 and the adsorbate 304 (e.g. $CO_2$). New chemical bonds 306 are generated at the adsorbant surface 302. The strong interaction between the adsorbate 304 and the substrate surface 302 creates new types of electronic bonds.

In some embodiments, the adsorption system further separates the carbon dioxide rich stream into a substantially pure carbon dioxide stream and a carbon dioxide-depleted stream by electric swing adsorption. As described in detail with reference to FIG. 6, an adsorption system that utilizes an electric swing adsorption can be compact and flexible, obviates the need for ancillary equipment, and eliminates the parasitic energy losses by using electrochemically activated redox carriers. The adsorption system can include an apparatus including a porous dielectric adsorbent material in between and in electrical communication with a first electrical conductor and a second electrical conductor.

Figure 4:
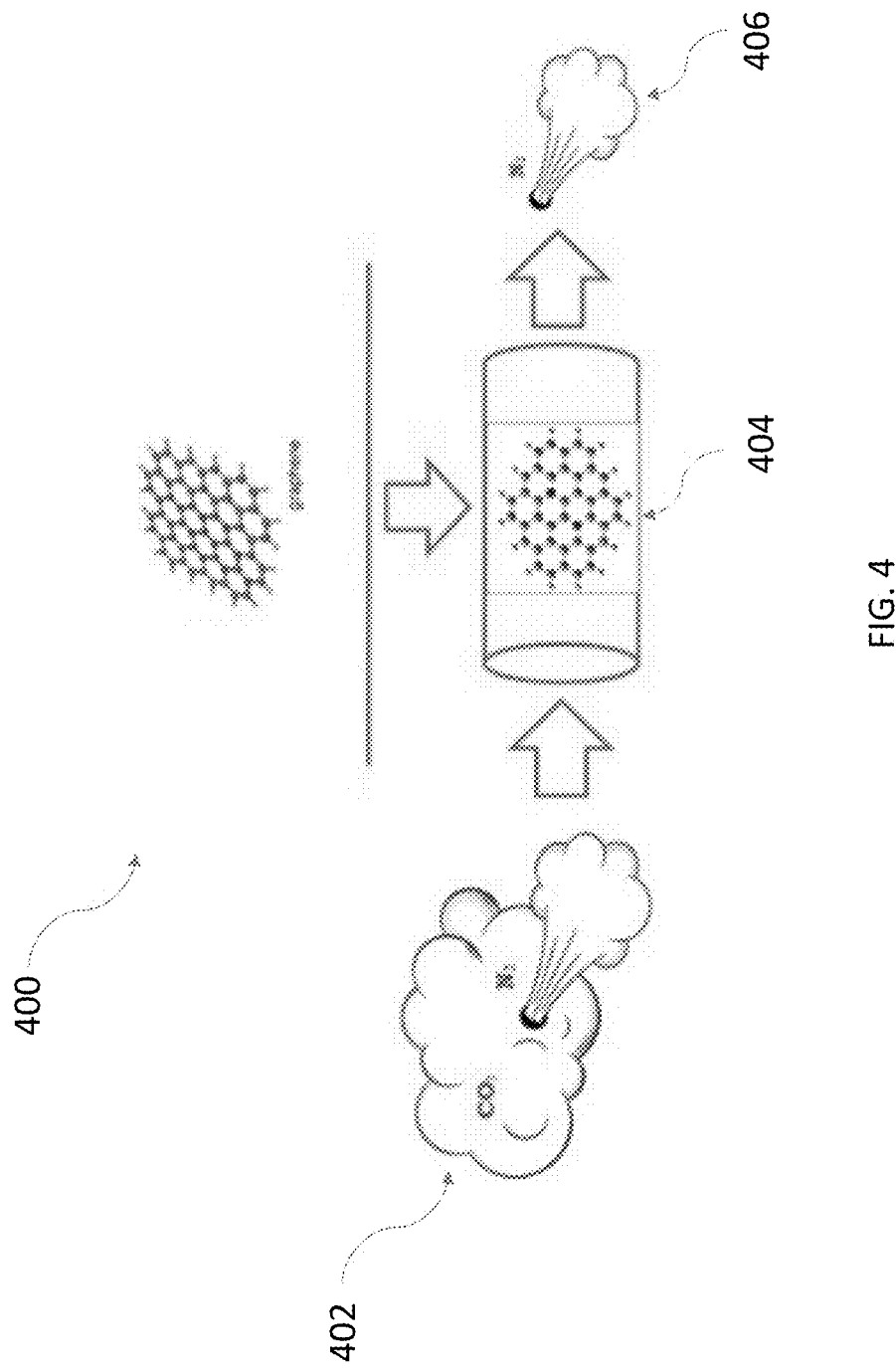
FIG. 4 illustrates a schematic view of a graphene membrane, according to an embodiment.

Referring now to FIG. 4, in some embodiments, a method 400 of removing carbon dioxide from a gas can include passing a gaseous feed stream 402 through a graphene-based membrane 404. In comparison with traditional chemical separation processes, membrane separation is much simpler and more efficient. An ideal membrane for molecular separation should be as thin as possible to maximize its solvent flux, be mechanically robust to prevent it from fracture, and have well-defined pore sizes to guarantee its selectivity. Graphene is an excellent platform for developing size-selective membranes because of its atomic thickness, high mechanical strength, and chemical inertness. The pore size of a graphene based membrane can be configured to include an optimized pore size carbon dioxide is allowed to pass through the membrane 404 while other larger molecules and/or particulates are filtered. In other embodiments, such as shown in FIG. 4, the $CO_2$ gas can be filtered allowing gasses 406 including smaller molecules such as $N_2$ and $H_2$ to pass through the membrane 404. The graphene-based membrane 404 can include at least one of a nanoporous single-layer graphene, a multi-layer graphene based stacked laminate, and/or a mixed-matrix membrane.

Figure 5C:
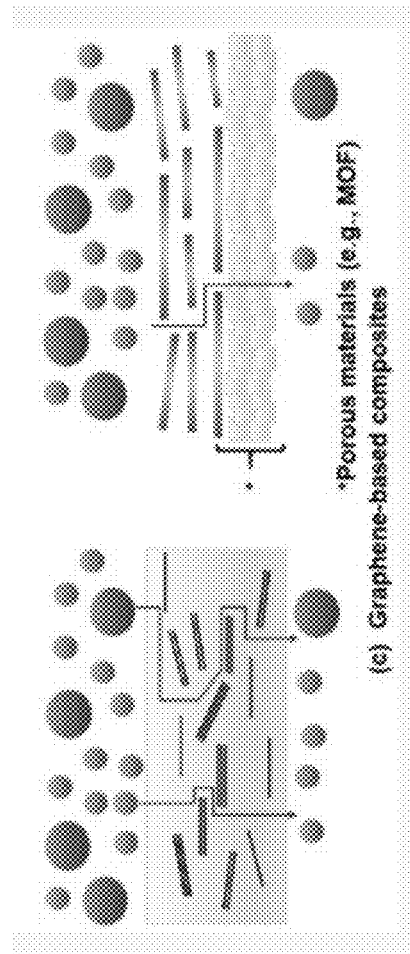
FIG. 5C illustrates a schematic of a mixed matrix membrane, according to an embodiment.
Figure 5A:
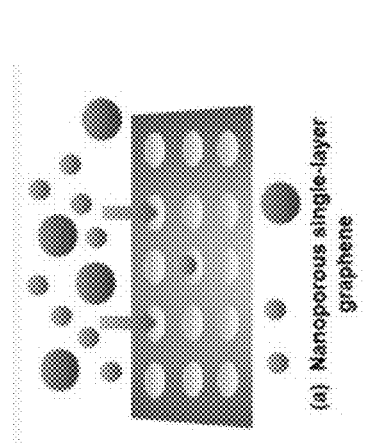
FIG. 5A illustrates a schematic of a nanoporous graphene membrane, according to an embodiment.

FIG. 5A illustrates a single-layer graphene. The monoatomic thickness of graphene-based materials gives theoretically the lowest transport resistance possible of a membrane. A defect-free single-layer graphene nanosheet is impermeable to gas molecules. To enable single-layer graphene as a membrane, there is a need to generate nanopores of optimized pore size for separation by a molecular sieving mechanism. There are several etching techniques used to generate nanopores on single-layer graphene nanosheet to date, including ion bombardment followed by chemical oxidation, focus-ion beam (FIB) patterning, gold nanoparticle deposition followed by oxidation, oxygen plasma with ozone etching, and ultraviolet-induced oxidative treatment. Each method utilizes etching to first create defects on the pristine single-layer graphene which can then be aggravated into nanopores. There appears no systematic control over the pores sizes by using different techniques.

Figure 5B:
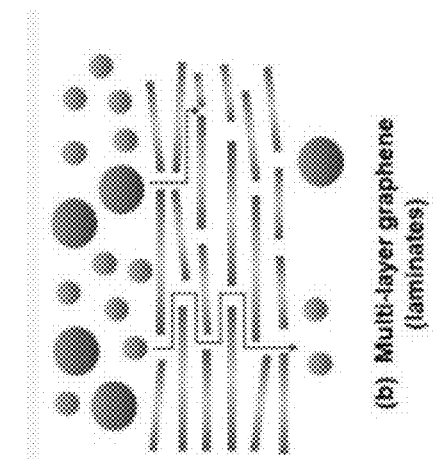
FIG. 5B illustrates a schematic of a multi-layer graphene-based stacked laminate, according to an embodiment.

FIG. 5B illustrates a multi-layer stacked graphene membrane. Relative to the single-layer graphene membrane, the few- to multi-layer stacked graphene-based laminates, with more than one layer of nanosheet, can form a continuous film. The requirement on the quality and integrity of the nanosheets is, therefore, less stringent for this type of membrane design. Membranes with few to multi-layer stacked graphene-based laminates can be prepared using graphene oxide (GO) nanosheets that are derived from the oxidation of graphite. GO-based stacked laminates are generally fabricated from a myriad of techniques, such as vacuum-assisted filtration, pressure-assisted filtration, spin-coating, spray-coating, dip-coating, shear-alignment, and layer-by-layer techniques. GO-based stacked laminates can range from a thickness of 1.8 nm (~3 layers of GO nanosheets) to several micrometers (multi-layered). The ideal thickness of the laminates can depend on the gas pairs to be separated and the target applications.

FIG. 5C illustrates a mixed-matrix membrane. Mixed-matrix membranes are defined when a solid phase filler material is added into a continuous matrix of polymer phase. In this context, the graphene-based materials serve as the filler materials. The rationale of doing so is to utilize the key attributes of the graphene-based materials to engineer the transport properties of the polymer matrix. The key attributes of graphene-based materials are their 2D morphologies and tunable physicochemical properties. The role of graphene-based materials in a mixed-matrix design is slightly different from the stacked laminates. At low loadings, the graphene-based materials capitalize on their well-defined interlayer spacing as low resistance nanochannels for diffusion of the smaller $CO_2$ molecules. At high loadings, however, the graphene-based fillers play a role that is similar to that of the stacked laminates. Mixed-matrix membranes are more cost-competitive as compared to graphene-based stacked laminates due to the smaller amount of graphene-based materials needed, as well as greater reliability in terms of mechanical properties and membrane performances given that the membranes include primarily of polymeric materials.

Figure 6:
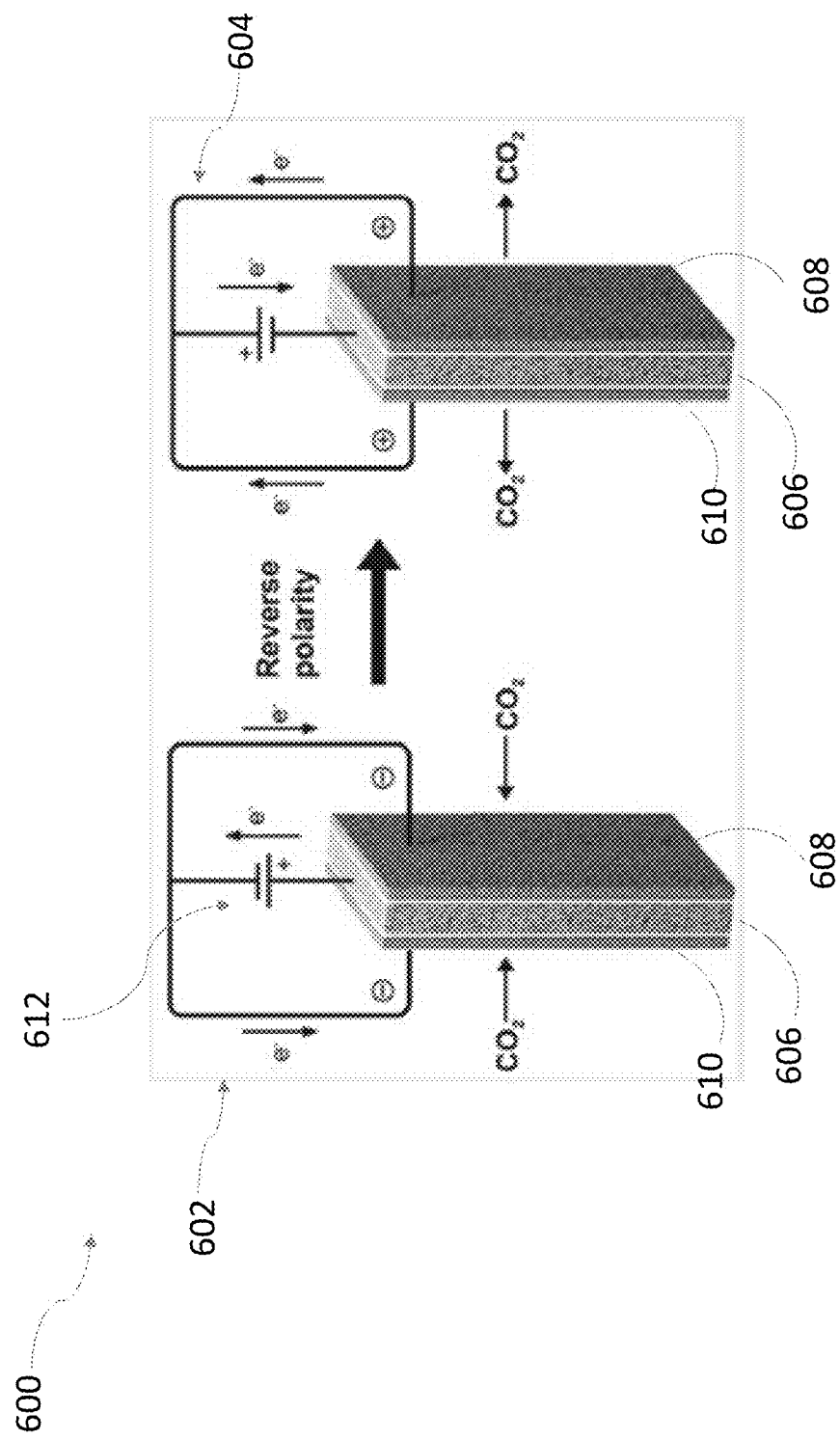
FIG. 6 illustrates a schematic of an adsorption system showing an electric swing adsorption, according to an embodiment.

The adsorbing and de-adsorbing of the carbon dioxide gas can be conducted by an electric swing adsorption. FIG. 6 illustrates an example electrochemical cell apparatus 600 for electric swing adsorption. When the electric swing cell charges (e.g. current is flowing through the cell), the carbon dioxide molecules are captured from the gaseous feed stream. When the electric swing cell discharges, the captured carbon dioxide is released. In FIG. 3, the diagram 602 shows the system being charged. The electric swing cell can include an apparatus including a porous dielectric adsorbent material 606 in between and in electrical communication with a first electrical conductor 608 and a second electrical conductor 610.

The power source 612 creates a voltage that causes electrons to flow from the dielectric adsorbent material 606 to the first or second electrical conductor 608, 610 through wires. In other words, an electric field is applied across the porous dielectric adsorbent material 606. The first or second electrical conductor 608,610 is now negatively charged. When $CO_2$-containing air or exhaust passes into the porous dielectric adsorbent material 606, the first electrical conductor 608 and the second electrical conductor 610 captures the $CO_2$ molecules until all the active sites on its surface are filled up. In some embodiments, the electric field can include an applied voltage from about 1V to about 3V. However the electric field can be between about 0.5V to about 5V, or other similar ranges.

The diagram 604 shows the discharge cycle. The direction of the voltage on the cell is reversed, and electrons flow from the first and second electrical conductors 608, 610 back to the porous dielectric adsorbent material 606. The first and second electrical conductors 608, 610 are no longer negatively charged, so have no affinity for $CO_2$. The $CO_2$ molecules can be released and removed out of the system/apparatus 600 by a stream of purge gas for subsequent use or disposal. The apparatus 600 is now regenerated and ready to capture more $CO_2$. Modulating the electric field strength by adjusting the applied voltage during gas loading and unloading allows direct control of gas uptake and release.

The application of the electric field across the porous dielectric adsorbent material 606 results in an increase in electrostatic binding forces between the porous dielectric adsorbent material 606 and the gas molecules within the material. The relative enhancement in binding is different for different gases. There is believed to be a physical basis for preferential binding of one gas with the porous dielectric adsorbent material 606 compared to that for another gas. The interaction between the gas and porous dielectric adsorbent material 606 is believed to be strongest at localized regions of high polarizability that enhance gas binding at those sites in the porous dielectric adsorbent material 606. Binding can be enhanced through both induction and dispersion forces. The applied field can also enhance binding interactions among the gas molecules themselves. For example, if the gas is carbon dioxide, application of the electric field can enhance the formation of carbon dioxide clusters in the dielectric by increasing dispersion and quadrupole-quadrupole interactions among the $CO_2$ molecules. When the applied electric field is removed, the induced electrostatic moment that stabilizes the gas dissipates. Thus, the thermodynamic driving force for binding can be switched on and off. As a result, the uptake/release dynamics do not depend only on thermal diffusion because much of the energy for binding and releasing the gas is reversibly (or near reversibly) introduced in the form of electrical work.

In some embodiments, the dielectric adsorbent material 606 includes a non-conductive insulator. Carbon itself does not conduct electricity, but its allotrope graphite does. Most of the carbon compounds do not conduct electricity because they have low melting and boiling points. Nature of bonding in carbon compounds is different from that observed in ionic compounds, thus they are poor conductors of electricity. In some embodiments, a composite of carbon can be processed such that the dielectric adsorbent material 606, the first electrical conductor 308, the second electrical conductor 610 include allotropes of carbon. The composite can include a nonconductive core of carbon with a graphene outer surface.

The use of the electric field to adjust and enhance adsorption provides higher efficiency, fast cycling and response times, reduced thermal management requirements, lower capital costs, and smaller process footprints because it applies energy directly to the molecules being separated, concentrated, and/or stored whereas other current mechanisms (pressure swing adsorption and temperature swing adsorption) apply the requisite energy across the bulk of the gas phase and adsorbent material. Some energy dissipation to heat can be expected upon executing a charge-discharge cycle, due to dielectric losses.

Figure 7:
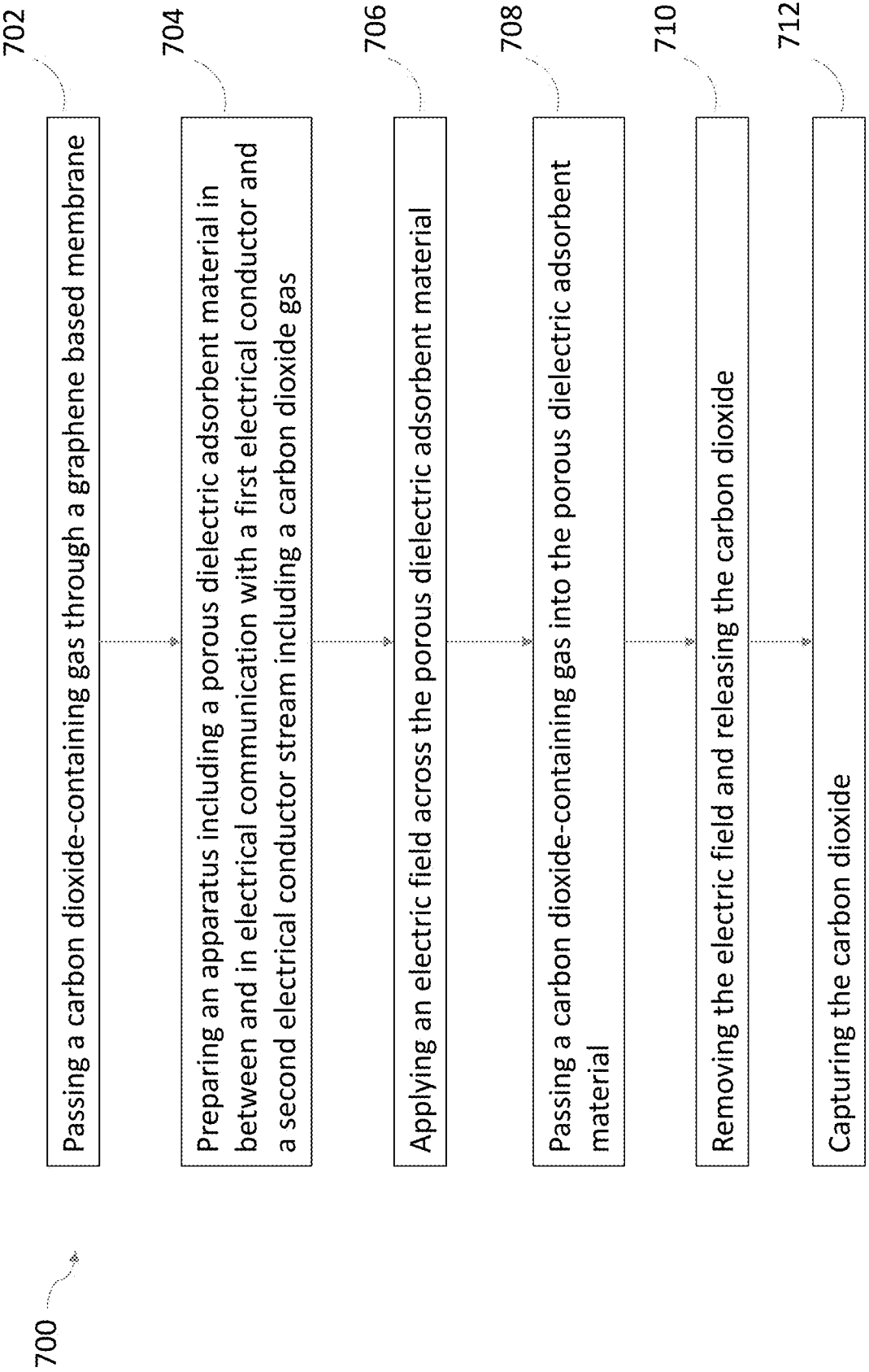
FIG. 7 illustrates a process flow diagram of a method of producing carbon dioxide, according to an embodiment.

Referring now to FIG. 7, a method 700 of producing carbon dioxide can include an act 702 of passing a carbon dioxide-containing gas through a graphene-based membrane. The graphene-based membrane can be at least one of a nanoporous single-layer graphene, a multi-layer graphene-based stacked laminate, and a mixed-matrix membrane, as described above. The method of producing carbon dioxide can also include an act 704 of preparing an apparatus including a porous dielectric adsorbent material in between and in electrical communication with a first electrical conductor and a second electrical conductor. In some embodiments, the first electrical conductor and the second electrical conductor can include a carbon-based material (e.g. graphene). The method of producing carbon dioxide can further include an act 706 of applying an electric field across the porous dielectric adsorbent material and passing the carbon dioxide-containing gas into the porous dielectric adsorbent material, wherein the carbon dioxide couples to the first electrical conductor and the second electrical conductor. The method can then include an act 710 of removing the electric field and releasing the carbon dioxide and then an act 712 of capturing the carbon dioxide.

In some embodiments, the electric field includes an applied voltage from about 1V to about 3V. The dielectric adsorbent material can include a non-conductive insulator. In some embodiments, the non-conductive insulator can include an allotrope of carbon. In other embodiments, the insulator can include air. In some embodiments, capturing the carbon dioxide can include combining the carbon dioxide with a substantially pure hydrogen gas to produce at least one methane and/or methanol.

Unless otherwise indicated, all numbers or expressions, such as those expressing dimensions, physical characteristics, etc., used in the specification (other than the claims) are understood as modified in all instances by the term "about." At the very least, and not as an attempt to limit the application of the doctrine of equivalents to the claims, each numerical parameter recited in the specification or claims which is modified by the term "about" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of about 1 to about 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

The invention claimed is:

1. A method of removing carbon dioxide from a gas, comprising:
   providing a gaseous feed stream including a carbon dioxide gas;
   adsorbing the carbon dioxide gas with a porous carbon sorbent comprising a graphene-based membrane consisting of a nanoporous single-layer graphene;
   de-adsorbing the carbon dioxide; and combining the carbon dioxide with a hydrogen gas to produce at least one of methane or methanol.

2. The method of claim 1, wherein the gaseous feed stream includes at least one of a flue gas, an exhaust, or a furnace exhaust.

3. The method of claim 1, wherein the porous carbon sorbent includes a mesoporous structure.

4. The method of claim 1, wherein the porous carbon sorbent includes an activated carbon including at least one of an activated carbon fiber, an activated graphene, a bituminous-coal-based activated carbon, an activated charcoal, or a coal composite.

5. The method of claim 1, wherein the porous carbon sorbent includes a carbon foam comprising an activated pitch.

6. The method of claim 1, wherein combining the carbon dioxide with a hydrogen gas is conducted in the presence of a catalyst.

7. The method of claim 6, wherein the catalyst includes at least one of molybdenum sulfide, ruthenium, or copper.

8. The method of claim 1, wherein the adsorbing and de-adsorbing of the carbon dioxide gas is conducted by an electric swing adsorption.

\* \* \* \* \*